(12) United States Patent
Voegele

(10) Patent No.: US 7,766,843 B2
(45) Date of Patent: Aug. 3, 2010

(54) BIOPSY METHOD

(75) Inventor: James W. Voegele, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 285 days.

(21) Appl. No.: 11/369,100

(22) Filed: Mar. 3, 2006

(65) Prior Publication Data
US 2007/0208271 A1     Sep. 6, 2007

(51) Int. Cl.
*A61B 10/00*     (2006.01)
(52) U.S. Cl. ..................................... 600/567
(58) Field of Classification Search ............... 600/562, 600/564, 566, 567, 568; 606/167, 170
See application file for complete search history.

(56) References Cited

U.S. PATENT DOCUMENTS

| | | | |
|---|---|---|---|
| 2,597,258 A | 5/1952 | Papp | |
| 3,537,451 A | 11/1970 | Beck et al. | |
| 4,651,752 A | 3/1987 | Fuerst | |
| 4,958,625 A | 9/1990 | Bates et al. | |
| 5,009,640 A | 4/1991 | Pyret et al. | |
| 5,106,364 A | 4/1992 | Hayafuji et al. | |
| 5,195,533 A * | 3/1993 | Chin et al. | 600/567 |
| 5,256,149 A | 10/1993 | Banik et al. | |
| 5,267,970 A | 12/1993 | Chin et al. | |
| 5,313,958 A * | 5/1994 | Bauer | 600/567 |
| 5,394,887 A | 3/1995 | Haaga | |
| 5,460,185 A | 10/1995 | Johnson et al. | |
| 5,526,822 A | 6/1996 | Burbank et al. | |
| 5,649,547 A | 7/1997 | Ritchart et al. | |
| 5,733,297 A | 3/1998 | Wang | |
| 5,769,086 A | 6/1998 | Ritchart et al. | |
| 5,775,333 A | 7/1998 | Burbank et al. | |
| 5,817,033 A | 10/1998 | Desantis | |
| 5,916,175 A | 6/1999 | Bauer | |
| 5,928,164 A | 7/1999 | Burbank et al. | |
| 5,944,673 A | 8/1999 | Gregoire | |
| 5,964,716 A | 10/1999 | Gregoire et al. | |
| 5,980,469 A | 11/1999 | Burbank et al. | |
| 5,989,196 A | 11/1999 | Chu et al. | |
| 6,007,497 A | 12/1999 | Huitema | |
| 6,017,316 A | 1/2000 | Ritchart et al. | |
| 6,077,230 A | 6/2000 | Gregoire et al. | |
| 6,086,544 A | 7/2000 | Hibner et al. | |

(Continued)

FOREIGN PATENT DOCUMENTS

DE     19703418     9/1997

(Continued)

OTHER PUBLICATIONS

Weisbrod et al, Preliminary Experience with a Dual Cutting Edge Needle in Thoracic Percutaneous Fine-Needle Aspiration Biopsy, Radiology 1987; 163:75-78.*

(Continued)

*Primary Examiner*—Max Hindenburg
*Assistant Examiner*—Brian Szmal

(57) ABSTRACT

A biopsy method is disclosed. The biopsy method can be used to provide a fine needle aspiration sample and a core biopsy sample. The biopsy method can include adjusting a sample port length without removing the biopsy device from the patient.

9 Claims, 3 Drawing Sheets

U.S. PATENT DOCUMENTS

| | | | |
|---|---|---|---|
| 6,120,462 | A | 9/2000 | Hibner et al. |
| 6,142,955 | A | 11/2000 | Farascioni et al. |
| 6,165,136 | A | 12/2000 | Nishtala |
| 6,217,548 | B1 | 4/2001 | Tsugita et al. |
| 6,228,055 | B1 | 5/2001 | Foerster et al. |
| 6,231,522 | B1 | 5/2001 | Voegele et al. |
| 6,244,447 | B1 | 6/2001 | Frieze et al. |
| 6,273,862 | B1 | 8/2001 | Privitera et al. |
| 6,283,925 | B1 * | 9/2001 | Terwilliger ............... 600/568 |
| 6,471,700 | B1 | 10/2002 | Burbank et al. |
| 6,485,436 | B1 | 11/2002 | Truckai et al. |
| 6,749,576 | B2 | 5/2004 | Bauer et al. |
| 7,419,472 | B2 | 9/2008 | Hibner et al. |
| 7,517,322 | B2 | 4/2009 | Weikel, Jr. et al. |
| 2003/0060817 | A1 | 3/2003 | Sauvageau et al. |
| 2003/0153926 | A1 | 8/2003 | Schmieding et al. |
| 2003/0163062 | A1 | 8/2003 | Bauer |
| 2003/0181897 | A1 | 9/2003 | Thomas et al. |
| 2003/0199753 | A1 | 10/2003 | Hibner et al. |
| 2004/0153003 | A1 | 8/2004 | Cicenas et al. |
| 2004/0167434 | A1 | 8/2004 | Fisher |
| 2005/0065453 | A1 | 3/2005 | Shabaz et al. |
| 2005/0215921 | A1 | 9/2005 | Hibner et al. |
| 2005/0283069 | A1 | 12/2005 | Hughes et al. |
| 2006/0200041 | A1 * | 9/2006 | Weikel et al. ............... 600/566 |
| 2006/0200042 | A1 | 9/2006 | Weikel, Jr. et al. |
| 2007/0208271 | A1 | 9/2007 | Voegele |
| 2007/0208272 | A1 | 9/2007 | Voegele |

FOREIGN PATENT DOCUMENTS

| | | |
|---|---|---|
| DE | 19709224 | 7/2001 |
| DE | 20209530 | 10/2002 |
| DE | 20209525 | 12/2002 |
| EP | 1698282 | 6/2006 |
| EP | 1698283 | 6/2006 |
| WO | 96/24289 | 8/1996 |
| WO | 98/50083 | 5/1997 |
| WO | WO 98/52502 A | 11/1998 |
| WO | 99/00966 | 1/1999 |
| WO | WO 2004/075719 A | 9/2004 |

OTHER PUBLICATIONS

EP Search Report dated Jul. 16, 2007 for corresponding patent application, European Patent Application No. 07250896.3 (END5378).

Office Action in U.S. Appl. No. 11/369,163, filed Jun. 11, 2008.

Response in U.S. Appl. No. 11/369,163, filed Oct. 10, 2008.

Preliminary Experience with a Dual Cutting Edge Needle in Thoracic Percutaneous Fine-Needle Aspiration Biopsy 1; Gordon L Weisbrod, MD FRCP et al. pp. 75-78; Radiology Apr. 1987.

EnCor MRI Specifications and Breast Biopsy System, SenoRx, (2005) p. 102.

European Search Report dated Aug. 1, 2006, for Application No. 06 25 1160.

European Search Report dated Aug. 1, 2006 for Application No. 06 25 1159.

European Search Report Communication dated Jul. 24, 2008 for Application No. 06 251 160.5.

Chinese Search Report dated Dec. 26, 2008 for Application No. 200610058114.7.

European Search Report Communication dated Mar. 24, 2009 for Application No. 06 251 159.7.

* cited by examiner

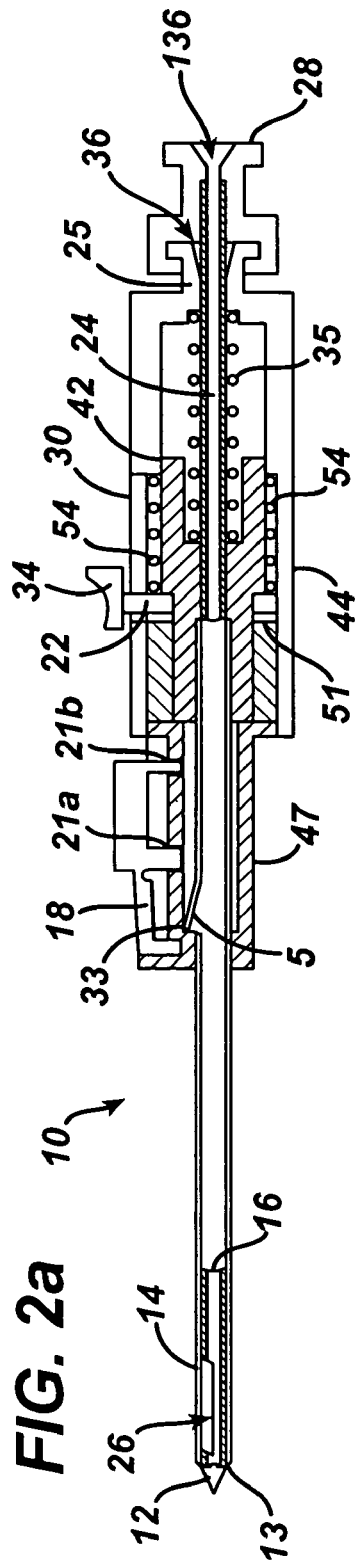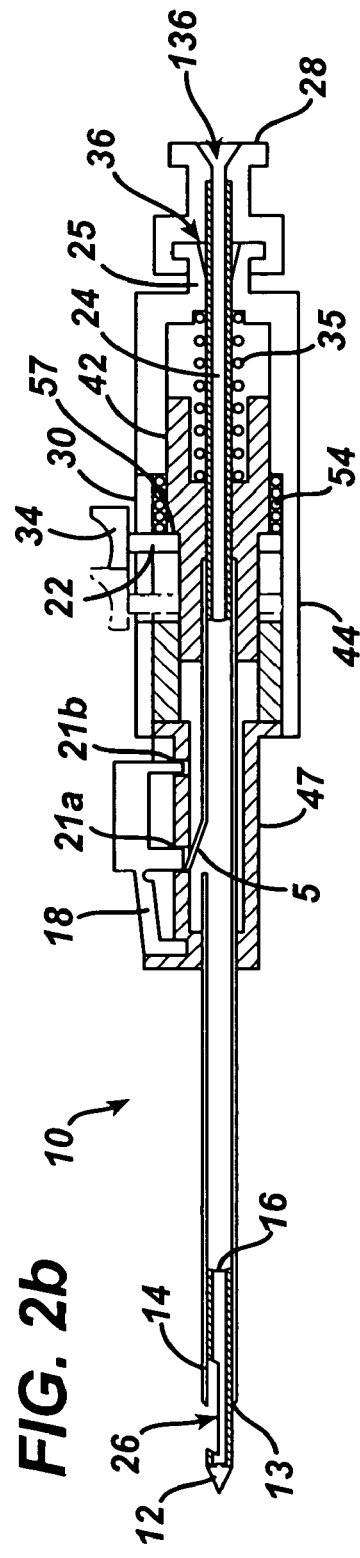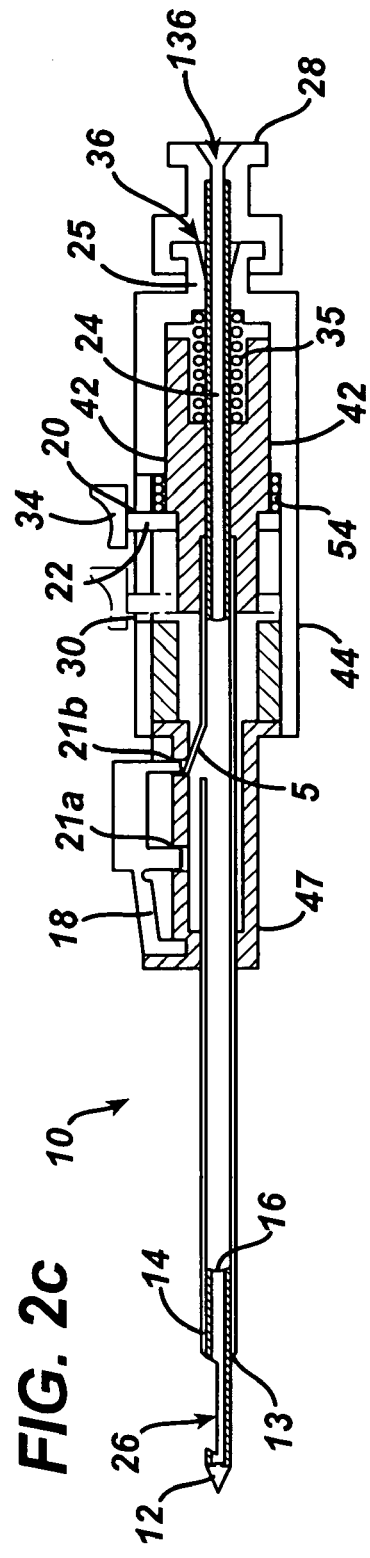

BIOPSY METHOD

This patent application cross references and incorporates by reference the following copending, commonly assigned patent applications: U.S. patent application Ser. No. 11/072, 719 filed Mar. 4, 2005 in the names of Weikel et al.; and U.S. patent application Ser. No. 11/222,575 filed Sep. 9, 2005 in the names of Weikel et al.

This patent application cross references and incorporates by reference commonly assigned patent application "Biopsy Device" filed on the same day herewith and in the name of Voegele.

FIELD OF THE INVENTION

The present invention is directed to a biopsy method, and more particularly, to a biopsy method which can be used to obtain both fine needle aspiration and core samples.

BACKGROUND OF THE INVENTION

A biopsy may be performed in various ways, including by taking a fine needle aspiration (FNA) sample or, alternatively, a core sample.

The diagnosis and treatment of tissue is an ongoing area of investigation. Medical devices for obtaining tissue samples for subsequent sampling and/or testing are know in the art. For instance, a biopsy instrument now marketed under the tradename MAMMOTOME is commercially available from Ethicon Endo-Surgery, Inc. for use in obtaining breast biopsy samples.

The following patent documents disclose various biopsy devices and are incorporated herein by reference in their entirety: U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996, and US Patent Application 2003/0199753 published Oct. 23, 2003 to Hibner et al.

Researchers in the medical device area continue to seek new and improved methods and devices for cutting, handling, and storing tissue samples.

SUMMARY OF THE INVENTION

Applicant has recognized the desirability of providing a biopsy method that can provide a fine needle aspiration (FNA) sample or a core sample. A surgeon may find one biopsy method to be unacceptable, necessitating a change to the alternative method. The present invention recognizes the desirability of biopsy method that can be employed to provide either a fine needle aspiration sample or a core sample. A method is disclosed that combines fine needle aspiration (FNA) and core biopsy capability. This combination of biopsy techniques can be accomplished, in part, by adjusting a sample window. The FNA biopsy can be performed using a pulling action to scrape/capture cells, which is a safer procedure than pushing an open end cutting tube as in conventional FNA procedures.

In one embodiment, the present invention provides a biopsy method. The method can include the steps of: providing an outer cannular cutter; providing an inner cannula having a side sample port; completely covering the side sample port with the outer cannula; inserting a distal portion of the inner cannula and the covered sample port into tissue to be sampled; and partially, but not fully uncovering the sample port by retracting the outer cannula relative to the inner cannula while the distal portion of the inner cannula is inserted in tissue. The method can include the steps of taking both an FNA sample and a core biopsy sample without removing the inner cannula from the tissue mass being sampled.

BRIEF DESCRIPTION OF THE FIGURES

FIG. 2a is a side cross sectional view of the biopsy device of FIG. 1 configured for insertion into tissue.

FIG. 2b is a side cross sectional view of the biopsy device of FIG. 1 configured to have the side tissue sample port partially uncovered for fine needle aspiration (FNA).

FIG. 2c is a side cross sectional view of the biopsy device of FIG. 1 configured to have the side tissue port uncovered for core sampling.

DETAILED DESCRIPTION OF THE INVENTION

Figure 1:
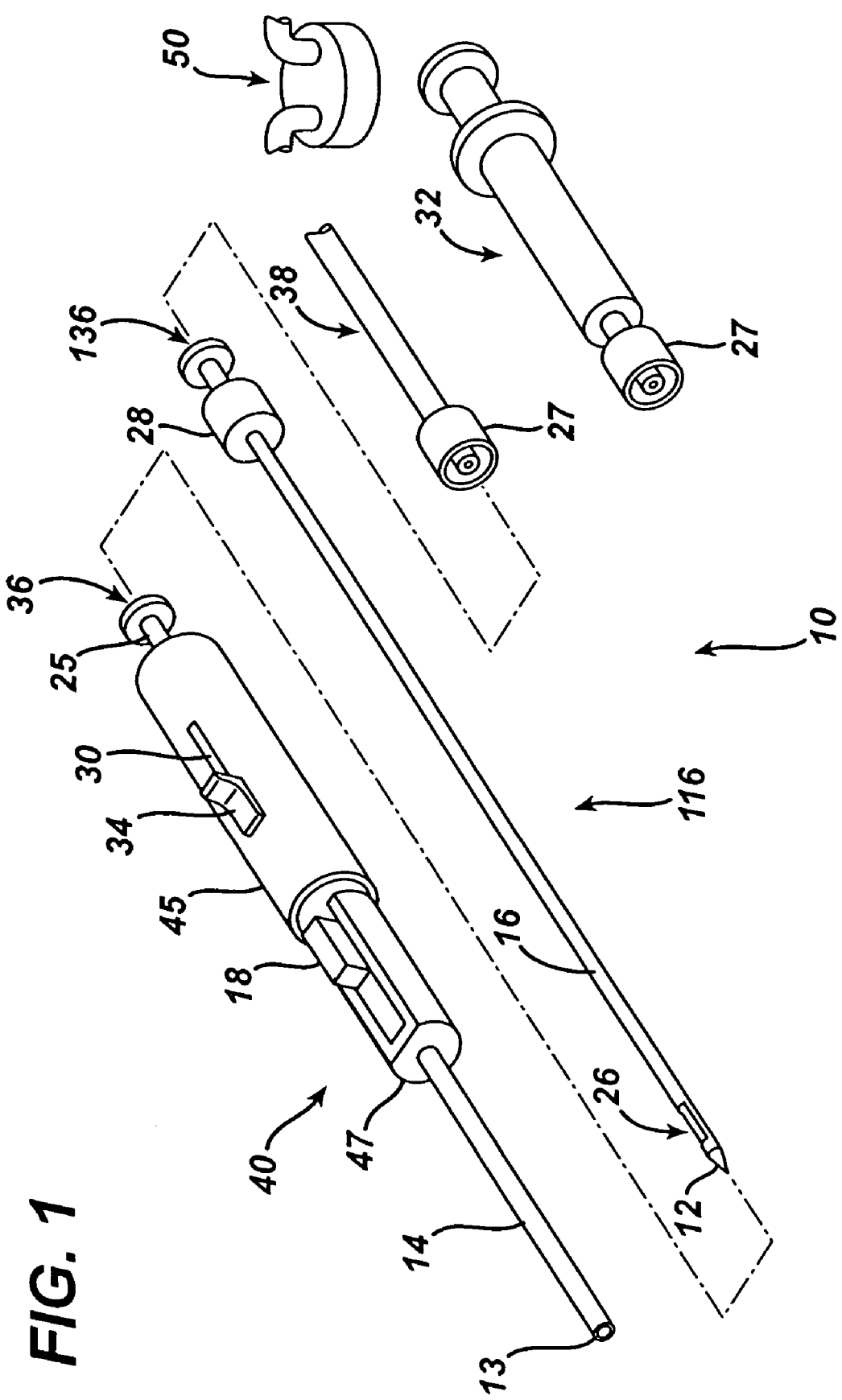
FIG. 1 is an isometric exploded view of a biopsy device according to one embodiment of the present invention.

FIG. 1 illustrates a biopsy device 10 useful in the biopsy method according to one embodiment of the present invention. Biopsy device 10 can include an outer sheath assembly 40 and an inner cannula assembly 116. The outer sheath assembly 40 can include an outer cannula 14, a body 47, and a handle 45. A proximal opening 36 can be provided in the proximal end of handle 45.

The inner cannula assembly 116 can include an inner cannula 16 extending distally from an inner cannula locking hub 28. A proximal opening 136 can be provided in the proximal end of inner cannula assembly 116. Referring to FIG. 1, a vacuum tube 38, a syringe 32, a sample/fluid capture container 50, or other suitable device may be releasably attached to the proximal end of the inner cannula assembly 116, such as by using a locking hub 27 associated with the device.

Inner cannula 16 can include a closed, distal tissue penetrating tip 12 adapted for piercing tissue. Inner cannula 16 can also include a side tissue sample port 26 disposed proximally of tip 12. Sample port 26 can communicate with a central lumen extending the length of cannula 16 to the proximal opening 136.

The outer cannula 14 can be supported to extend distally through at least a portion of body 47. Body 47 can extend distally from handle 45. A biopsy method selection button 34 can be provided on handle 45, and a release button 18 can be provided on body 47. The biopsy method selection button can be used to select a fine needle aspiration mode of operation or a core sample mode of operation. Release button 18 can be used to release the position of outer cannula 14, as described more fully below.

Proximal opening 36 allows for insertion of inner cannula 16 into outer sheath assembly 40. The relative position of inner cannula 16 to outer sheath assembly 40 can be maintained in a plurality of positions to provide a desired biopsy sampling mode. For instance, the relative position of inner cannula 16 to outer sheath assembly 40 can be maintained by a locking outer hub 28 disposed a proximal end of inner cannula 16. Locking hub 28 can be shaped or otherwise configured to releasably engage an inner hub 25 associated with a proximal end of the handle 45. For instance, hub 25 can be received in a distal end of hub 28 to provide releasable attachment using any suitable latching or locking mechanism, including without limitation Leur type fittings, bayonet fittings, and the like.

FIG. 2a illustrates a cross section of biopsy device 10 in position for insertion into tissue. In FIG. 2a, the inner cannula 16 is shown inserted within the outer sheath assembly 40, and with outer hub 28 releasably coupled to the inner hub 25. Outer cannula 14 can extend distally from a cannula carrier 42. Cannula carrier 42 is shown disposed within handle 45 in FIG. 2a and can be biased distally relative to the handle 45, such as by a resilient member disposed intermediate carrier 42 and an inner surface of handle 45. In FIG. 2a, the resilient member comprises a coil spring 35 seated in a proximal facing recess in carrier 42 and a distal facing recess in the inner surface of handle 45. As shown in FIG. 2a, the inner cannula 16 can extend through spring 35 when the inner cannula 16 is inserted into outer sheath assembly 40.

The proximal end of cannula 14 can be disposed in a central opening in the distal face of the carrier 42, with the outer cannula 14 extending from the distal face of cannula carrier 42, The cannula 14 can be attached to carrier 42 by any suitable means, including without limitation by adhesives or interference fit. As shown in FIG. 2a, a tab 5 can be provided on cannula 14. Tab 5 can be formed from a section of wall of outer cannula 14, such as by milling or otherwise cutting or forming a slot in the wall of cannula 14 and bending a portion of the wall back to form a resilient tab 5. Spring 35 biases tab 5 distally against a shoulder 33 formed in a passageway extending through body 47. Various alternatives to a cut tab 5 can be employed, such as a separate resilient tab joined to the outer surface of cannula 14, or a resilient rib or projection formed to extend from the outer surface of cannula 14.

Referring to FIGS. 2a, 2b, and 2c, the body 47 can include slots 21a and 21b, with slot 21b being positioned proximally of slot 21a. In the embodiment shown, the slots 21a and 21b extend through the thickness of the wall of body 47. Tab 5 of outer cannula 14 is positionable in slot 21a for fine needle aspiration, and is positionable in slot 21b for core biopsy sampling. Tab 5 is shown positioned in slot 21a in FIG. 2b, and tab 5 is shown positioned in slot 21b in FIG. 2c.

In the insertion position illustrated in FIG. 2a, tab 5 of outer cannula 14 is biased against shoulder 33 of body 47, and the outer cannula 14 completely covers sampling port 26 preventing tissue from entering the sample port during insertion or removal of the device. Outer cannula 14 can have an open distal end with a shaped distal edge 13. The sharpened distal edge 13 of outer cannula 14 can be disposed just proximal of tip 12 when inner cannula 16 is inserted fully into outer cannula 14. The distal edge 13 can include a generally conical, tapered surface which can serve to provide an extension of the sloped surface of tip 12 when the inner cannula 16 is inserted fully into outer cannula 14. The outer diameter of inner cannula 16 can be selected to slide freely within the lumen of outer cannula 14. Outer cannula 14 can be provided with an outer diameter corresponding to any size of biopsy needle. Common biopsy needle sizes range from 8 gauge to 25 gauge.

FIG. 2b illustrates the biopsy device 10 in position for obtaining a fine needle aspiration (FNA) sample. In the FNA position illustrated in FIG. 2b, outer cannula 14 is retracted proximally relative to inner cannula 16 a distance less than the longitudinal length of sample port 26, in order to expose a portion, but not all of, the longitudinal length of sample port 26. This position is accomplished by pushing selection button 34 (mounted on the outer surface of handle 45) proximally in button slot 30 (such as with an operator's thumb) formed in the outer surface of handle 45, until tab 5 resiliently snaps into slot 21a.

Selection button 34 can include a ring 22 that slip fits over an outer surface of a circular section of the distal end of cannula carrier 42, such that ring 22 can slide freely with respect to the carrier 42 and the handle 45. A coil spring 54 can be provided to resiliently bias the ring 22 and button 34 in a distal direction. The coil spring 54 can be disposed about an outer surface of the proximal portion of carrier 42. As shown in FIGS. 2a, 2b, and 2c, the proximal end of spring 54 can be seated against a shoulder formed on an inner surface of the handle 45, and the coil spring 54 can bear against a proximal face of ring 22, such that removal of a thumb force on selection button 34 permits spring 54 to urge ring 22 distally to its default position at a proximal end surface 51 of body 47. The carrier 42 and outer cannula 14 will remain in the position shown in FIG. 2a until release button 18 is depressed and releases tab 5 from slot 21a. Release of tab 5 enables main spring 35 to push cannula carrier 42 and outer cannula 14 to close sample port 26.

A Fine Needle Aspiration (FNA) sample is obtained by withdrawing a sample of cells (as distinguished from a solid tissue sample) from a lump, cyst, fluid filled sac, or other suspicious lesion. To collect an FNA sample, the device can be positioned as shown in FIG. 2b, and the user can reciprocate the exposed portion of sample port 26 (such as in a back and forth motion) within the tissue mass, to thereby scrape cells from the target tissue mass. If desired, the tissue cells received in sample port 26 can be drawn into port 26 by vacuum communicated through cannula 16. For example, vacuum can be provided by a syringe 32 (FIG. 1) which may be releasably attached to opening 136.

FIG. 2c illustrates the biopsy device 10 in position for obtaining a core biopsy sample. In the core biopsy position, outer cannula 14 can be retracted to expose the entire sample port 26, as shown in FIG. 2c. To retract outer cannula 14, the selection button 34 can be moved proximally (by a finger of the hand holding the handpiece 40) within button slot 20 until tab 5 snaps into slot 21b. Moving selection button 34 proximally (against the biasing force of spring 54) within button slot 20 causes outer cannula 14 to move proximally, against the biasing force of spring 35, to fully expose sample port 26. With the sample port 26 fully exposed, a vacuum can be applied through inner cannula 16 drawing the tissue into sample port 26. In order to sever a core sample of tissue, the operator can depress release button 18 to release tab 5 from slot 21b. Releasing tab 5 from slot 21b enables spring 35 to push cannula carrier 42 and outer cannula 14 distally, thereby closing sample port 26. As outer cannula 14 moves over sample port 26, the distal cutting edge 13 of outer cannula 14 cuts through the tissue mass, severing a core tissue sample disposed in sample port 26.

Figure 3:
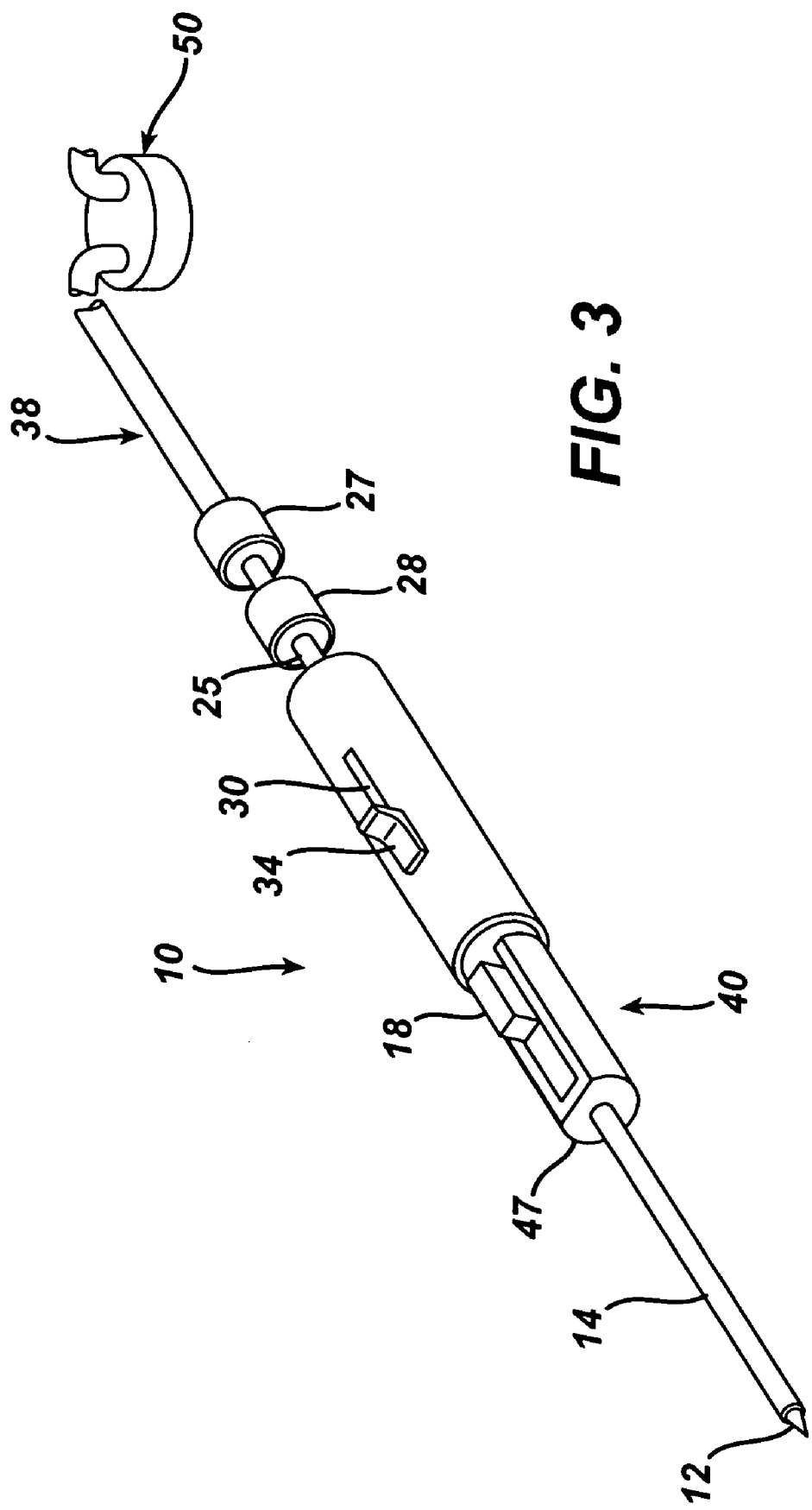
FIG. 3 is an isometric view of the biopsy device of FIG. 1 assembled and with a vacuum tube attached.

FIG. 3 discloses various components according one embodiment of biopsy device 10. Biopsy device 10 is shown with vacuum tube 38 connected at a proximal end of the device to provide vacuum to inner cannula 16 through opening 136. Vacuum tube 38 allows for application of a vacuum through inner cannula 16 to assist in drawing cells (in FNA procedure) or tissue (in core procedure) into sample port 26.

With biopsy device 10 in the insertion position shown in FIG. 2a, the surgeon inserts the distal end of the biopsy device 10 into the tissue mass to be sampled. The surgeon can, depending on the preferred method of biopsy, use the same device to obtain either an FNA sample, or a core biopsy sample. For an FNA sample, selection button 34 is pushed proximally in button slot 30 until tab 5 snaps into slot 21a. The surgeon moves tip 12 over tissue to scrape cells from the tissue mass. If desired, the surgeon can employ the device 10 under any suitable visualization method, including without limitation, X-ray, ultrasound, or Magnetic Resonance Imaging (MRI). For instance the components of the biopsy device can be formed of suitable MRI compatible materials for use with MRI devices. The cells are pulled into partially covered sample port 26 by vacuum (such as vacuum generated by a syringe 32.

After the FNA sample is taken from the tissue mass, the surgeon may desire to obtain either another FNA sample, or alternatively, a core biopsy sample, such as from the same tissue mass from which the FNA sample was taken. The surgeon can obtain a second sample, such as a core biopsy sample, without removing the device from the tissue mass, and without employing a different or additional biopsy device. For instance, to retrieve a second sample, the surgeon can push selection button 34 proximally into button slot 20 until tab 5 snaps into slot 21*b*, so that the sample port 26 is fully open. Release button 18 can then be depressed so that outer cannula 14 is biased distally to slide over sample port 26, thereby cutting through the tissue mass and severing a core tissue sample disposed in sample port 26. Upon completion of the biopsy, outer cannula 14 can be returned to insertion position and the surgeon removes biopsy device 10 from patient.

In one embodiment, the sample port 26 can have an uncovered length, as measured along the length of cannula 16, of at least about 10 millimeters, and more particularly, at least about 20 millimeters. In the FNA position shown in FIG. 2*b*, the sample port can be uncovered to provide a side tissue inlet port having a length of no more than about 5 millimeters, and more particularly, no more than about 3 millimeters. In the core biopsy position shown in FIG. 2*c*, the sample port 26 can be fully uncovered to provide a side tissue inlet port having a length of at least about 10 millimeters, and more particularly at least about 20 millimeters.

The biopsy device shown in FIGS. 2*a*-2*c* provides two distinct, predetermined positions of the outer cannula 14 relative to sample port 26, one position corresponding to FNA sampling, and one position corresponding to core tissue sampling. While the biopsy device shown in FIGS. 2*a*-2*c* employs two slots 21*a* and 21*b*, it will be understood that more than two slots can be provided to accommodate three or more positions of the outer cannula 14 relative to the sample port 26, so that graduated exposure of the sample port 26 is obtained. Additionally, mechanisms other than slots 21 can be employed to provide positioning of cannula 14 relative to sample port 26.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The various components and subassemblies disclosed herein can be described in the alternative as a means for providing the function performed by the particular component or subassembly. While the present invention has been described in terms of the embodiments disclosed in the figures, it will be understood that those skilled in the art may make various changes and modifications without departing from the spirit and scope of the present invention. Accordingly, the above description is not intended to limit the scope of the present invention, and it will be understood that the scope of the present invention is defined in terms of the claims set forth below.

What is claimed:

1. A biopsy method comprising the steps of:
providing an outer cannular cutter;
providing an inner cannula having a side sample port;
covering the side sample port with the outer cannular cutter;
inserting a distal portion of the inner cannula with the covered sample port into tissue to be sampled;
partially, but not fully uncovering the sample port by retracting the outer cannular cutter relative to the inner cannula while the distal portion of the inner cannula is inserted in tissue, wherein the longitudinal position of the inner cannula is substantially fixed during the act of partially, but not fully uncovering the sample port; and
taking a first biopsy sample through the sample port, wherein the longitudinal position of the inner cannula is substantially fixed during the act of taking a first biopsy sample;
drawing at least a portion of the tissue sample through the inner cannula; and
taking a second biopsy sample without removing the outer cannular cutter or the inner cannula from the tissue being sampled.

2. The biopsy method of claim 1 wherein the step of inserting the distal portion of the inner cannula comprises inserting the distal portion of the inner cannula into breast tissue.

3. The biopsy method of claim 1 further comprising the step of communicating a source of vacuum with the internal cannula.

4. The biopsy method of claim 1 further comprising the step of scraping a distal portion of the inner cannula against tissue to dislodge cells for sampling.

5. The biopsy method of claim 4 further comprising the step of drawing the dislodged cells through the inner cannula using vacuum.

6. The biopsy method of claim 1 wherein the step of partially uncovering the side sample port comprises uncovering the side sample port to provide a port length of no more than about 3 mm.

7. The biopsy method of claim 1 comprising taking a fine needle aspiration sample and a core biopsy sample without removing the inner cannula from the tissue being sampled.

8. The biopsy method of claim 1 wherein the step of partially uncovering the side sample port comprises uncovering the side sample port to provide a port length of no more than about 5 mm to obtain the first biopsy sample, and wherein the method further comprises uncovering the side sample port to provide a port length of at least about 10 mm to provide the second sample.

9. The biopsy method of claim 1 wherein the step of partially uncovering the side sample port comprises uncovering the side sample port to provide a port length of no more than about 3 mm to obtain the first biopsy sample, and wherein the method further comprises uncovering the side sample port to provide a port length of at least about 20 mm to provide the second sample.

* * * * *